(12) United States Patent
Brown et al.

(10) Patent No.: US 6,613,951 B1
(45) Date of Patent: *Sep. 2, 2003

(54) PROCESS FOR CONVERTING METHANOL TO OLEFINS

(75) Inventors: Stephen H. Brown, Princeton, NJ (US); Reuel Shinnar, Great Neck, NY (US); William A. Weber, Marlton, NJ (US)

(73) Assignee: Mobil Oil Corporation, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/401,078

(22) Filed: Sep. 23, 1999

(51) Int. Cl.⁷ .............................. C07C 1/20; C07C 1/207
(52) U.S. Cl. ....................................... 585/640; 585/639
(58) Field of Search .................. 585/634, 640; 502/71, 77, 208

(56) References Cited

U.S. PATENT DOCUMENTS

| | | | |
|---|---|---|---|
| 3,911,041 A | 10/1975 | Kaeding et al. | 260/682 |
| 4,044,065 A | 8/1977 | Butter et al. | 260/677 R |
| 4,049,573 A | 9/1977 | Kaeding | 252/432 |
| 4,088,706 A | 5/1978 | Kaeding | 260/688 R |
| 4,480,145 A | 10/1984 | Brennan et al. | 585/640 |
| 4,499,314 A | 2/1985 | Seddpm et al. | 585/408 |
| 4,849,573 A | 7/1989 | Kaedoing | 585/640 |
| 5,171,921 A | 12/1992 | Gaffaey et al. | 585/653 |
| 5,278,345 A | 1/1994 | Janssen et al. | 585/640 |
| 6,046,372 A | * 4/2000 | Brown et al. | 585/640 |
| 6,506,954 B1 | * 1/2003 | Brown et al. | 585/640 |
| 6,538,167 B1 | * 3/2003 | Brown et al. | 585/640 |

FOREIGN PATENT DOCUMENTS

| | | | |
|---|---|---|---|
| EP | 0 123 449 | 10/1984 | |
| FR | 2 285 176 | 4/1976 | B01J/29/28 |
| WO | WO 99 51549 | 10/1999 | C07C/1/00 |

* cited by examiner

Primary Examiner—Thuan D. Dang
(74) Attorney, Agent, or Firm—Paul T. LaVoie

(57) ABSTRACT

There is provided a process for converting methanol or dimethyl ether to a product containing $C_2$ to $C_4$ olefins, which comprises the step of contacting a feed containing methanol or dimethyl ether with a catalyst which comprises a zeolite having 10-ring intersecting channels, such as ZSM-5, and which has a Diffusion Parameter for 2,2-dimethylbutane of less than 100 $sec^{-1}$ when measured at a temperature of 120° C. and a 2,2-dimethylbutane pressure of 60 torr (8 kPa). The contacting step is conducted at a temperature of 370 to 480° C., a methanol partial pressure of 30 to 150 psia and a methanol conversion per pass of less than 95%.

8 Claims, 3 Drawing Sheets

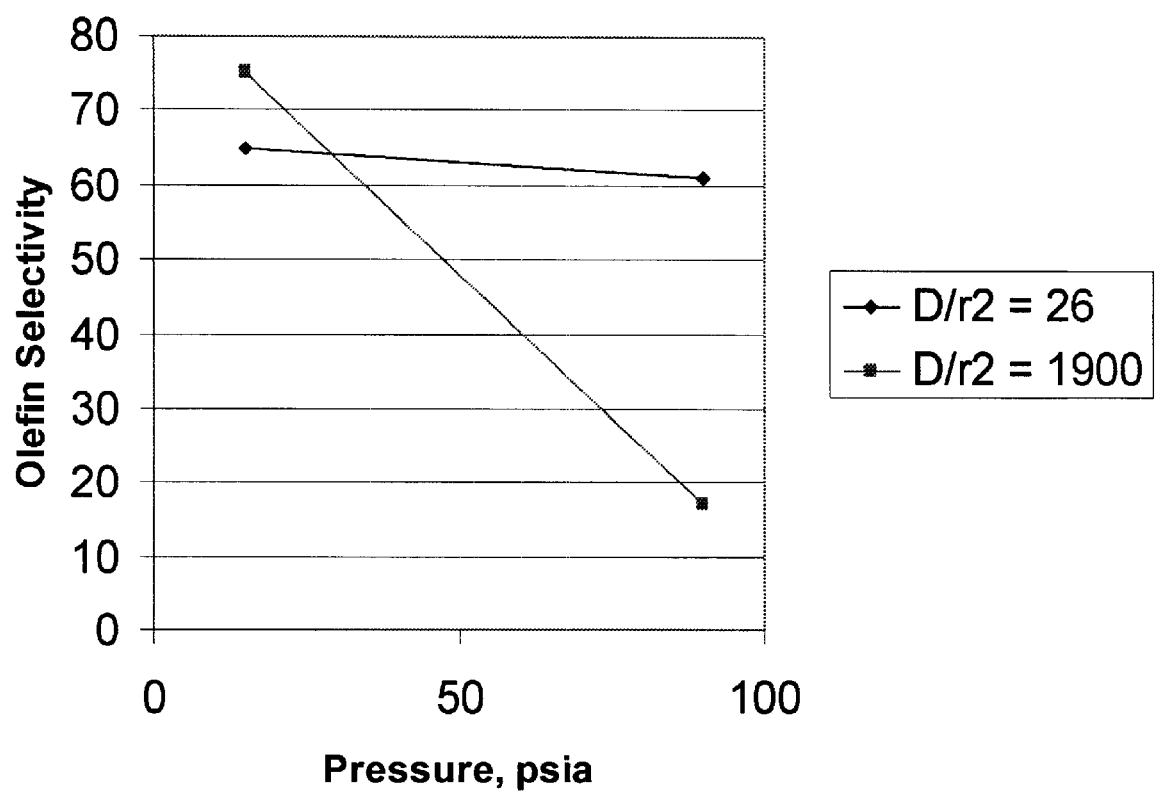

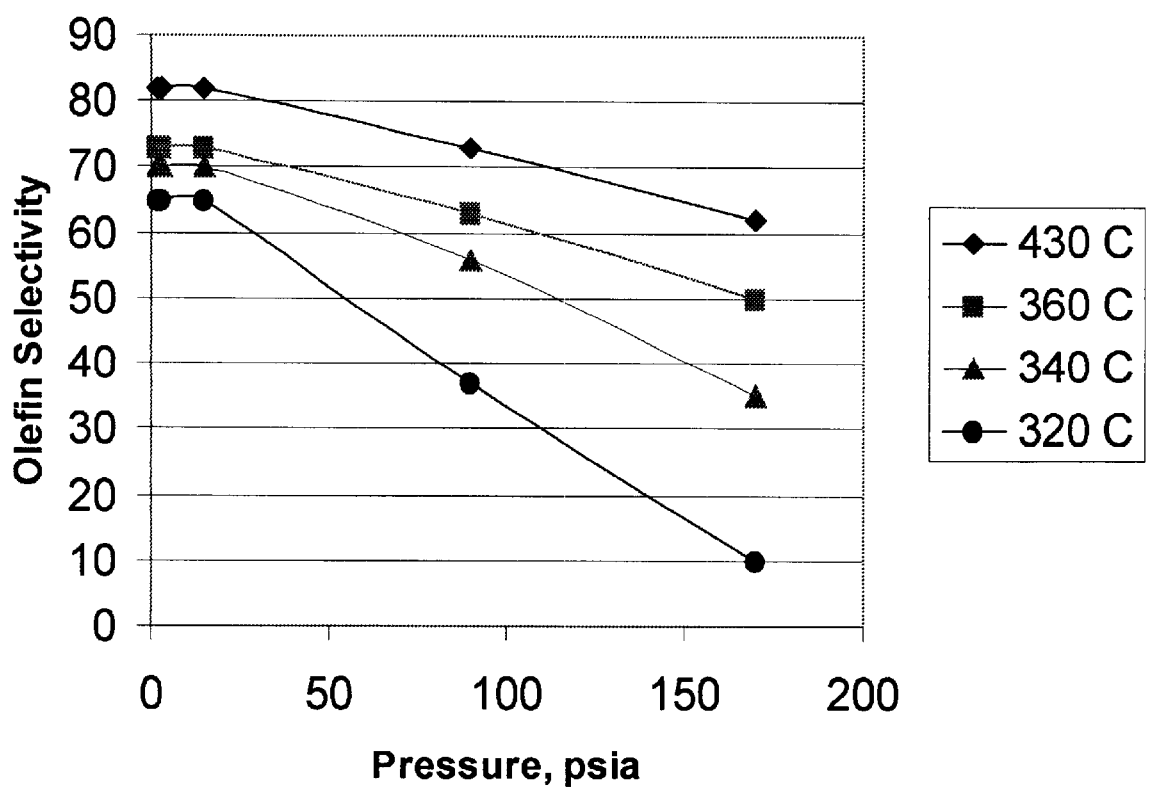

PROCESS FOR CONVERTING METHANOL TO OLEFINS

FIELD OF THE INVENTION

The present invention relates to a process for converting methanol and/or dimethyl ether to olefins, particularly light olefins rich in ethylene and propylene.

BACKGROUND TO THE INVENTION

There is a growing need for light olefins, especially ethylene and propylene, for a variety of uses making it desirable to develop sources of the olefins additional to the conventional source, crude oil. One such additional source is methanol and/or dimethyl ether which can be catalytically converted over certain zeolite catalysts to olefin-containing hydrocarbon mixtures.

For example, U.S. Pat. No. 3,911,041 discloses that methanol can be converted to $C_2$–$C_4$ olefins by contacting the methanol at a temperature of 300–700° C. with a crystalline aluminosilicate zeolite catalyst which has a Constraint Index of 1–12, such as ZSM-5, and which contains at least about 0.78% by weight of phosphorus incorporated in the crystal structure of the zeolite.

U.S. Pat. Nos 4,049,573 and 4,088,706 disclose that methanol can be converted to a hydrocarbon mixture rich in $C_2$–$C_3$ olefins and mononuclear aromatics, a, particularly p-xylene, by contacting the methanol at a temperature of 250–700° C. and a pressure of 0.2 to 30 atmospheres with a crystalline aluminosilicate zeolite catalyst which has a Constraint Index of 1–12 and which has been modified by the addition of an oxide of boron or magnesium either alone or in combination or in further combination with oxide of phosphorus.

U.S. Pat. No. 4,480,145 discloses that the ethylene yield in the catalytic conversion of methanol over ZSM-5 can be increased by moderating the diffusivity of the zeolite by the use of the large crystal form of the zeolite and by silica "stuffing" of the zeolite pores. This patent also discloses that by steaming the zeolite at 180–820° C. to reduce its alpha activity to 6–10 the cycle life and methanol conversion activity of the zeolite can be increased. The reaction conditions employed in this patent are a temperature of 260–400° C. and a pressure of 1 to 10 atmospheres.

U.S. Pat. No. 4,849,573 teaches that the use of zeolites with a Constraint Index of 1–12 and a silica to alumina molar ratio of 298 to 2000 increases the light olefin yield when methanol is converted to hydrocarbons at a temperature of 350–700° C. and a pressure of 1 to 100 atmospheres.

U.S. Pat. No 4,499,314 discloses that the addition of various promoters, including aromatic compounds, such as toluene, accelerate the conversion of methanol to hydrocarbons over zeolites, such as ZSM-5, which have a pore size sufficient to permit sorption and diffusion of the promoter. In particular, the '314 patent teaches that the increased conversion resulting from the addition of the promoter allows the use of lower severity conditions, particularly lower temperatures, which increase the yield of lower olefins (column 4, lines 17–22). Thus in Example 1 of the patent the addition of toluene as a promoter reduces the temperature required to achieve full methanol conversion from 295° C. to 288° C. while increasing the ethylene yield from 11 wt % to 18 wt %. In the Examples of the '314 patent the methanol feedstock is diluted with water and nitrogen such that the methanol partial pressure is less than 2 psia.

The '314 patent is representative of the current expectation in the art that, in the conversion of methanol over zeolites, such as ZSM-5, the overall selectivity decreases as the partial pressure of methanol is increased and that ethylene selectivity is reduced as the temperature is increased. Thus attempts to maximize ethylene selectivity have focussed on systems operating at low temperature, below 350° C., and low methanol partial pressure, below atmospheric. Unfortunately, however, operation at low methanol partial pressure necessarily reduces the perpass ethylene yield and hence the overall efficiency of the process.

Unexpectedly, it has now been found that by using a zeolite having 10-ring intersecting channels, such as ZSM-5, in a catalyst with reduced diffusion characteristics and by operating within narrowly defined, but relatively high temperatures and pressures, methanol can be converted with a high selectivity and yield of $C_2$ to $C_4$ olefins, particularly to ethylene.

SUMMARY OF THE INVENTION

The invention resides in a process for converting methanol or dimethyl ether to a product containing $C_2$ to $C_4$ olefins, the process comprising the step of contacting a feed containing methanol or dimethyl ether with a catalyst which comprises a zeolite having 10-ring intersecting channels and which has a Diffusion Parameter for 2,2-dimethylbutane of less than 100 $\text{sec}^{-1}$ when measured at a temperature of 120° C. and a 2,2-dimethylbutane pressure of 60 torr (8 kPa), the contacting step being conducted at a temperature of 370 to 480° C., a methanol partial pressure of 30 to 150 psia.

Preferably, the catalyst has a Diffusion Parameter of about 0.1–30 $\text{sec}^{-1}$.

Preferably, the contacting step is operated so that the methanol conversion per pass is 25–90%.

Preferably, the catalyst contains an oxide of phosphorus.

Preferably, the catalyst contains about 0.05 to about 20 wt %, and more preferably about 1 to about 10 wt %, of said oxide phosphorus on an elemental basis.

Preferably, the zeolite is ZSM-5.

BRIEF DESCRIPTION OF THE INVENTION

FIG. 2 is a graph of comparing the total olefin selectivity against methanol partial pressure for the process of Example 1 with that of Example 2 (Comparative); and FIG. 3 is a graph of total olefin selectivity against methanol partial pressure at various temperatures in the process of Example 4.

DETAILED DESCRIPTION OF THE INVENTION

Figure 1:
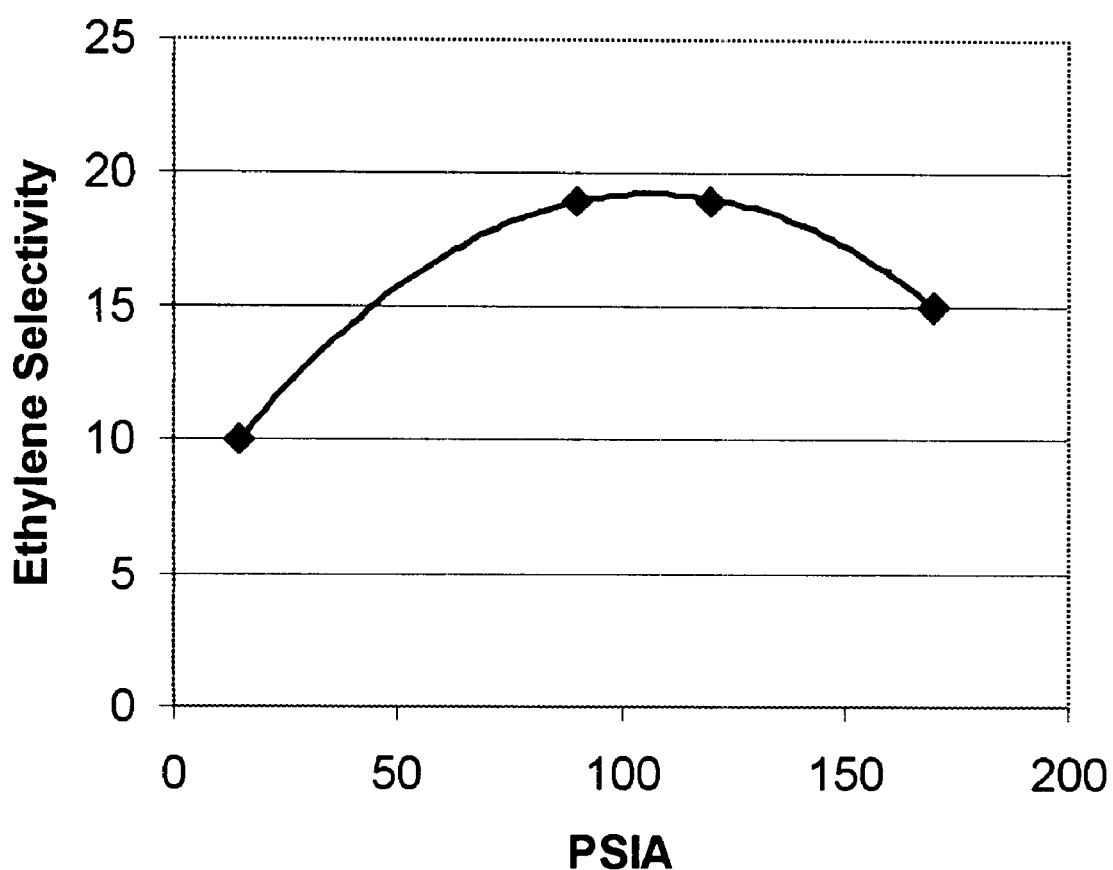
FIG. 1 is a graph of ethylene selectivity against methanol partial pressure for the process of Example 1.

The present invention provides a process for selectively converting methanol or dimethyl ether to $C_2$–$C_4$ olefins, and particularly ethylene, using a catalyst which comprises a zeolite having 10-ring intersecting channels and which has a Diffusion Parameter for 2,2-dimethylbutane less than 30 $\text{sec}^{-1}$, preferably 0.2–10 $\text{sec}^{-1}$, when measured at a temperature of 120° C. and a 2,2-dimethylbutamine pressure of 60 torr (8 kPa).

As used herein, the Diffusion Parameter of a particular porous crystalline material is defined as $D/r^2 \times 10^6$, wherein D is the diffusion coefficient ($\text{cm}^2/\text{sec}$) and r is the crystal radius (cm). The required diffusion parameters can be derived from sorption measurements provided the assumption is made that the plane sheet model describes the diffusion process. Thus for a given sorbate loading Q, the value $Q/Q_\infty$, where $Q_\infty$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

The catalyst employed in the process of the invention comprises a zeolite which has 10-ring intersecting channels. Suitable zeolites include ZSM-5 and ZSM-11, with ZSM-5 being particularly preferred. Zeolite ZSM-5 and the conventional preparation thereof are described in U.S. Pat. No. 3,702,886, the disclosure of which is incorporated herein by reference. Zeolite ZSM-11 and the conventional preparation thereof are described in U.S. Pat. No. 3,709,979, the disclosure of which is incorporated herein by reference.

As conventionally prepared catalysts containing ZSM-5 and ZSM-11 have a Diffusion Parameter for 2,2-dimethylbutane significantly in excess of 30 sec$^{-1}$, and typically in excess of 1000 sec$^{-1}$. However, the diffusivity required for the catalyst of the invention can be produced by a variety of previously disclosed synthetic strategies. One method to achieve the diffusivity required for the catalyst of the invention is severely steaming the catalyst so as to effect a controlled reduction in the micropore volume of the catalyst to not less than 50%, and preferably to 50–90%, of that of the unsteamed catalyst. Reduction in micropore volume is derived by measuring the n-hexane adsorption capacity of the catalyst, before and after steaming, at 90° C. and 75 torr n-hexane pressure. Steaming is effected at a temperature of at least about 850° C., preferably about 950 to about 1075° C., and most preferably about 1000 to about 1050° C. for about 10 minutes to about 10 hours, preferably from 30 minutes to 5 hours To effect the desired controlled reduction in micropore volume and diffusion parameter, it may be desirable to combine the catalyst, prior to steaming, with a phosphorus modifier. The amount of phosphorus modifier, as measured on an elemental basis, may be between about 0.05 and about 20 wt. %, and preferably is between about 1 and about 10 wt. %, based on the weight of the final catalyst.

Incorporation of the phosphorus modifier into the catalyst of the invention is conveniently achieved by the methods described in U.S. Pat. Nos. 4,356,338, 5,110,776 and 5,231,064, the entire disclosures of which are incorporated herein by reference. Treatment with phosphorus-containing compounds can readily be accomplished by contacting the porous crystalline material, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt. %.

Representative phosphorus-containing compounds which may be used include derivatives of groups represented by $PX_3$, $RPX_2$, $R_2PX$, $R_3P$, $X_3PO$, $(XO)_3PO$, $(XO)_3P$, $R_3P=O$, $R_3P=S$, $RPO_2$, $RPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as phenyl radical, and X is hydrogen, R, or halide. These compounds include primary, $RPH_2$, secondary, $R_2PH$, and tertiary, $R_3P$, phosphines such as butyl phosphine, the tertiary phosphine oxides, $R_3PO$, such as tributyl phosphine oxide, the tertiary phosphine sulfides, $R_3PS$, the primary, $RP(O)(OX)_2$, and secondary, $R_2P(O)OX$, phosphonic acids such as benzene phosphonic acid, the corresponding sulfur derivatives such as $RP(S)(SX)_2$ and $R_2P(S)SX$, the esters of the phosphonic acids such as dialkyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites, and esters thereof such as the monopropyl ester, alkyl dialkylphosphinites, $(RO)PR_2$, and dialkyl alkyphosphinite, $(RO)_2PR$, esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$, and $(RS)_2PR$. Examples of phosphite esters include trimethylphosphite, triethylphosphite, diisopropylphosphite, butylphosphite, and pyrophosphites such as tetraethylpyrophosphate. The alkyl groups in the mentioned compounds preferably contain one to four carbon atoms.

Other suitable phosphorus-containing compounds include ammonium hydrogen phosphate, the phosphorus halides such as phosphorus trichloride, bromide, and iodide, alkyl phosphorodichloridites, $(RO)PCl_2$, dialkylphosphoro-chloridites, $(RO)_2PCl$, dialkylphosphinochloroidites, $R_2PCl$, alkyl alkylphosphonochloridates, $(RO)(R)P(O)Cl$, dialkyl phosphinochloridates, $R_2P(O)Cl$, and $RP(O)Cl_2$. Applicable corresponding sulfur derivatives include $(RS)PCl_2$, $(RS)_2PCl$, $(RS)(R)P(S)Cl$, and $R_2P(S)Cl$.

Particular phosphorus-containing compounds include ammonium phosphate, ammonium dihydrogen phosphate, diammonium hydrogen phosphate, diphenyl phosphine chloride, trimethylphosphite, phosphorus trichloride, phosphoric acid, phenyl phosphine oxychloride, trimethylphosphate, diphenyl phosphinous acid, diphenyl phosphinic acid, diethylchlorothiophosphate, methyl acid phosphate, and other alcohol-$P_2O_5$ reaction products.

After contacting with the phosphorus-containing compound, the catalyst may be dried and calcined to convert the phosphorus to an oxide form. Calcination can be carried out in an inert atmosphere or in the presence of oxygen, for example, in air at a temperature of about 150 to 750° C., preferably about 300 to 500° C., for at least 1 hour, preferably 3–5 hours.

The zeolite employed in the process of the invention may be combined with a variety of binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of zeolite and inorganic oxide matrix vary widely, with the content of the former ranging from about 1 to about 90% by weight and more usually, particularly when the composite is prepared in the form of beads, in the range of about 2 to about 80 wt. % of the composite.

Preferably, the binder material comprises silica or a kaolin clay.

Procedures for preparing silica-bound zeolites, such as ZSM-5, are described in U.S. Pat. Nos. 4,582,815; 5,053,374; and 5,182,242. A particular procedure for binding ZSM-5 with a silica binder involves an extrusion process.

The porous crystalline material may be combined with a binder in the form of a fluidized bed catalyst. This fluidized bed catalyst may comprise clay in the binder thereof, and may be formed by a spray-drying process to form catalyst particles having a particle size of 20–200 microns.

The catalyst employed in the present invention preferably has a, very low acid activity. Using the alpha test of acid activity disclosed in *Journal of Catalysis*, volume 61, page 395 (1980) the catayst of the invention preferably has an alpha value less than 10, more preferably less than 5 and typically below 1. Preferably, the catalyst used in the process of the invention is characterized by an unusually high hydrothermal stability such that, after steaming the catalyst at 1025° C. for 45 minutes in 1 atmosphere steam, the catalyst exhibits a methanol conversion activity of at least 50% when contacted with methanol at a pressure of 1 atmosphere, a temperature of 430° C. and 0.5 WHSV, preferably at 1 WHSV and most preferably at 2 WHSV.

The process of the invention is preferably carried out in a moving or fluid catalyst bed with continuous oxidative regeneration. The extent of coke loading can then be continuously controlled by varying the severity and/or the frequency of regeneration.

The process of the present invention is conducted at a temperature of 360 to 480° C., a methanol partial pressure of 30 to 150 psia and a methanol conversion per pass of less than 95%. Preferably, the process is conducted at a temperature of 400 to 450° C., a methanol partial pressure of 60 to 120 psia and a methanol conversion per pass of 25–90%.

Any methanol feed comprising at least 60 wt % of methanol may be used to provide methanol for the use in the process of the invention. Substantially pure methanol, such as industrial grade anhydrous methanol, is eminently suitable. Crude methanol, which usually contains from 12 to 20 wt % water, or even a more dilute solution, may also be used. However, the presence of water as a diluent to reduce the methanol partial pressure is not required and in general is not preferred. Trace amounts (<1% by weight) of non-aromatic organic impurities, such as higher alcohols, aldehydes, or other oxygenated compounds have little effect on the conversion reaction of this invention and may be present in the methanol feed. In place of, or in addition to methanol, the feed may comprise dimethyl ether.

The feedstock may also comprise an aromatic compound which has a critical diameter less than the pore size of the zeolite catalyst and which is capable of alkylation by the methanol and/or dimethyl ether under said the conditions of the process. Suitable aromatic compounds include benzene, toluene, xylenes, C9+ reformate streams, light reformates, full-range reformates or any distilled fraction thereof, Coker naphtha or any distilled fraction thereof, FCC naphtha or any distilled fraction thereof, and coal derived aromatics. Where toluene comprises some or all of the aromatic compound, the process of the invention produces xylenes comprising a high proportion of the para isomer, in addition to the light olefins.

Where an aromatic compound is present, the molar ratio of methanol and/or dimethyl ether to aromatic compound will normally be greater than 5:1, and preferably from 5:1 to 150:1.

The process of the invention converts methanol and/or dimethyl ether to a light olefin stream in which ethylene comprises over 30 wt %, and typically over 40 wt %, of the $C_2$ to $C_4$ olefins and in which ethylene comprises more than 90 wt %, and preferably more than 95 wt %, of the $C_2$ component.

The invention will now be more particularly described with reference to the following Examples and the accompanying drawings in which:

FIG. 1 is a graph of ethylene selectivity against methanol partial pressure for the process of Example 1;

FIG. 2 is a graph of comparing the total olefin selectivity against methanol partial pressure for the process of Example 1 with that of Example 2 (Comparative); and FIG. 3 is a graph of total olefin selectivity against methanol partial pressure at various temperatures in the process of Example 4.

In the Examples, experiments were conducted in a downflow fixed-bed unit in which the 18", ½" O.D. quartz reactor with ⅛" O.D. internal quartz thermowell was centered inside a 10", single-zone furnace. Methanol and aromatic feedstocks were obtained from Aldrich and used as received. Distilled water was produced in-house. Feed was introduced using two high pressure-positive displacement pumps. Aromatics and methanol were blended in the desired molar ratio and delivered from one pump. The second pump was used to deliver the distilled water. 1/16" O.D. tubing was used to deliver each feedstock to a single, 250-cc vaporizer which was heat-traced and held at 220° C. Vaporized feed flowed from the vaporizer through the reactor, into a 300-cc product back-mixing vessel, through an on-line GC equipped with a 60-m DBWax column and an FID detector, and into a product collection can held at room temperature. Any gasses produced flowed through the product collection can and finally through a wet test meter. All feed and product lines upstream of the GC sampling were held above 200° C. using heat tracing. The unit backpressure was controlled with a Grove Loader. On-line total product GC was used to determine product composition.

Micropore volume (n-hexane) measurements were made on a computer controlled (Vista/Fortran) duPont 951 Thermalgravimetric analyzer. Isotherms were measured at 90° C. and adsorption values taken at 75 torr n-hexane. The diffusion measurements were made on a TA Instruments 2950 Thermalgravimetric Analyzer equipped with a Thermal Analysis 2000 controller, a gas switching accessory and an automatic sample changer. Diffusion measurements were made at 120° C. and 60 torr 2,2-dimethylbutane and data were plotted as uptake versus square root of time.

EXAMPLE 1

This example employed an FCC additive-type catalyst containing 450:1 $SiO_2:Al_2O_3$ molar ratio ZSM-5 in a binder to zeolite weight ratio of 60:40 and containing about 4 wt % P. The catalyst had been pre-steamed at 870° C. (1600° F.) for 4 hours such that the catalyst tested had an alpha of about 1, a diffusion parameter of 26, and a n-hexane sorption of 38 mg/g. The catalyst was used to convert methanol at 430° C. and 15, 90, 120, and 170 psia. Ethylene, propylene, C4+ and total olefin selectivities under each condition at a methanol conversion level of about 70°% are shown in Table 1. Ethylene selectivity vs. pressure is plotted in FIG. 1.

TABLE 1

| Pressure, psia | 15 | 90 | 120 | 170 |
|---|---|---|---|---|
| Temperature, ° C. | 430 | 430 | 430 | 430 |
| ZSM-5 d/r2 | 26 | 26 | 26 | 26 |
| MeOH Conversion | 70% | 70% | 70% | 70% |
| Selectivity, wt % of HC | | | | |
| Ethylene | 10 | 19 | 19 | 15 |
| Propylene | 24 | 15 | 15 | 12 |
| C4+ | 31 | 27 | 26 | 20 |
| total | 65 | 61 | 60 | 47 |

The results listed in Table 1 and plotted in FIG. 1 are unexpected and demonstrate that while, total olefin selectivity dropped by only 10%, ethylene selectivity increased by more than 60% by raising the reactor pressure from 15 to 90 psia methanol. This unexpected improvement in ethylene selectivity without excessive loss of overall olefin selectivity was demonstrated up to a methanol partial pressure of about 150 psia, but by 170 psia methanol pressure it will be seen that both the olefin and ethylene selectivity had decreased significantly. These results are important since ethylene is produced at progressively lower cost as reactor pressure rises.

EXAMPLE 2 (COMPARATIVE)

A ZSM-5 extrudate catalyst containing 65 wt % 55:1 $SiO_2:Al_2O_3$ molar ratio ZSM-5 and 35 wt % alumina binder was steamed at 787° C. for 45 minutes such that the steamed catalyst had an alpha of about 4, a diffusion parameter of 1900, and a n-hexane sorption of 35 mg/g. The steamed catalyst was used to convert methanol at 430° C. and 15 psia and 90 psia methanol partial pressure. Ethylene, propylene, C4+ and total olefin selectivities under each condition at a methanol conversion level of about 70% are shown in Table 2.

TABLE 2

| Pressure, psia | 15 | 90 |
|---|---|---|
| Temperature, ° C. | 430 | 430 |
| ZSM-5 d/r2 | 1900 | 1900 |
| MeOH Conversion | 70 | 70 |

TABLE 2-continued

| Selectivity, wt % of HC | | |
|---|---|---|
| Ethylene | 2 | 4 |
| Propylene | 25 | 7 |
| C4+ Olefins | 46 | 6 |
| Other HC's | 27 | 83 |
| Total olefins | 73 | 17 |

The results shown in Table 2 are as expected by those skilled in the art, namely that raising pressure using a ZSM-5 catalyst with conventional diffusivity dramatically reduces total olefin selectivity without improving ethylene selectivity.

FIG. 2 plots ethylene selectivity vs. pressure for the catalysts of Examples 1 and 2 and shows the unexpected result that olefin selectivity vs. pressure curves are a strong function of ZSM-5 diffusion parameter at 430° C.

EXAMPLE 3 (COMPARATIVE)

Phosphoric acid, kaolin clay, and 450:1 SiO2/Al2O3 ZSM-5 were slurried in water and spray dried to make a fluid—bed catalyst. The catalyst was calcined in air at 510° C. The finished catalyst contained 40 wt % ZSM-5 and 4.5 wt % phosphorus. This catalyst was then steamed at 1050° C. (1920° F.) for 0.75 h, after which treatment it had an alpha of about 1, a diffusion parameter of 0.5, and a n-hexane sorption of 31 mg/g. The catalyst was used to convert methanol at 480° C. and 15 psia and at 330° C. and 15 psia. Ethylene, propylene, C4+ and total olefin selectivities under each condition at a methanol conversion level of about 70% are shown in Table 3.

TABLE 3

| Pressure, psia | 15 | 15 |
|---|---|---|
| Temperature, ° C. | 330 | 480 |
| ZSM-5 d/r2 | 26 | 26 |
| MeOH Conversion | 70 | 70 |
| Selectivity, wt % of HC | | |
| Ethylene | 26 | 8 |
| Propylene | 21 | 30 |
| C4+ Olefins | 27 | 42 |
| Other HC's | 26 | 20 |
| Total olefins | 74 | 80 |

The data in Table 3 shows that, even with ZSM-5 catalysts having low diffusion parameters, ethylene selectivity at low methanol partial pressure decreases markedly as the temperature is increased. In contrast, according to the invention, it has been unexpectedly found that a combination of low diffusion parameter ZSM-5, high temperature, and high pressure unexpectedly leads to good selectivities to ethylene and propylene.

EXAMPLE 4

This Example employed a commercially available FCC additive catalyst containing 26:1 $SiO_2:Al_2O_3$ molar ratio ZSM-5 in a binder to zeolite weight ratio of 75:25 and containing about 3 wt % P. The catalyst had been pre-steamed at 790° C. (1450° F.) for 4 hours such that the catalyst tested had an alpha of about 3, a diffusion parameter of 25, and a n-hexane sorption of 25 mg/g. The catalyst was used to convert a mixture of 90 wt % methanol and 10 wt % toluene (methanol:toluene molar ratio of 26:1) at various temperatures and pressures.

The total olefin selectivity under each condition at a methanol conversion level of about 70% is shown in FIG. 3. It will seen from FIG. 3 that, with the toluene cofeed, at all the temperatures tested the total olefin selectivity is independent of pressure out to 15 psia then decreases with pressure out to 170 psia methanol partial pressure, with the decrease being less pronounced at 430° C. than at 320° C.

Table 4 lists the selectivities to ethylene, propylene, C4+olefins at increasing pressure and a constant temperature of 320° C. It will be seen that, at this low temperature even with the presence of the toluene cofeed, the ethylene and propylene selectivity decrease rapidly with increasing pressure.

TABLE 4

| Pressure, psia | 15 | 90 | 170 |
|---|---|---|---|
| Temperature, ° C. | 320 | 320 | 320 |
| ZSM-5 d/r2 | 26 | 26 | 26 |
| MeOH Conversion | 70 | 70 | 70 |
| Pdt Selectivity, wt % of HC | | | |
| Ethylene | 23 | 14 | 4 |
| Propylene | 16 | 7 | 3 |
| C4+ Olefins | 25 | 16 | 3 |
| Other HC's | 36 | 67 | 90 |
| Total olefins | 64 | 37 | 10 |

EXAMPLE 5

The catalyst from example 1 was used to convert methanol at 430° C. and 90 psia methanol partial pressure. The results are given in Table 5.

EXAMPLE 6

Phosphoric acid, kaolin clay, and 450:1 SiO2/Al2O3 ZSM-5 were slurried in water and spray dried to make a fluid—bed catalyst. The catalyst was calcined in air at 510° C. The finished catalyst contained 40 wt % ZSM-5 and 4.5 wt % phosphorus. This catalyst was then steamed at 1050° C. (1920° F.) for 0.75 h, after which treatment it had an alpha of about 1, a diffusion parameter of 0.5, and a n-hexane sorption of 31 mg/g. This catalyst was used to convert methanol at 430° C. and 90 psia. The hydrocarbon product selectivities are reported in Table 5.

TABLE 5

| Example | 5 | 6 | 6 |
|---|---|---|---|
| Pressure, psia | 90 | 90 | 90 |
| Temperature, ° C. | 430 | 430 | 430 |
| ZSM-5 d/r2 | 26 | 0.5 | 0.5 |
| MeOH Conversion | 80 | 80 | 99 |
| Selectivity, wt % of HC | | | |
| Ethylene | 17 | 20 | 17 |
| Propylene | 15 | 18 | 12 |
| p-xylene + p-ethyltoluene | 7 | 8 | 10 |
| Other | 61 | 54 | 61 |
| Total chemicals | 39 | 46 | 39 |

The examples of Table 5 are attractive targets for commercialization. Example 6 produces ample petrochemicals at attractive process conditions using a selectivated ZSM-5 catalyst. Most of the other hydrocarbons produced are conveniently converted to high octane gasoline. Example 5 produces more gasoline and less chemicals, but uses a less expensive catalyst.

EXAMPLE 7 (COMPARATIVE)

The catalyst of example 6 was used to convert methanol to hydrocarbons at 480° C. and 15 psia. Light olefin selectivities at a methanol conversion level of about 80% are shown in Table 6.

EXAMPLE 8 (COMPARATIVE)

A commercially available ZSM-5 catalyst, containing 65 wt % ZSM-5, that had been steamed at 790° C. (1450° F.) for 1 hour to an alpha of about 4, a diffusion parameter of 1883, and a n-hexane sorption of 62 mg/g, was used to convert methanol to hydrocarbons at 430° C. and 15 psia. Light olefin selectivities at a methanol conversion level of about 80% are shown in Table 6.

TABLE 6

| Example | 7 | 8 |
|---|---|---|
| Pressure, psia | 15 | 15 |
| Temperature, ° C. | 480 | 480 |
| ZSM-5 d/r2 | 0.5 | 1900 |
| Olefin Selectivity, wt % | | |
| Ethylene | 7 | 4 |
| Propylene | 31 | 29 |
| C4+ | 43 | 45 |
| total | 81 | 78 |

The results reported in Table 6 confirm that the products from methanol conversion at typical methanol to olefin conversion conditions are not dramatically different when catalysts of widely different d/r2 values are used. The results from the Examples reported in Tables 2, 4 and 6 confirm that elevation of pressure normally leads to dramatically reduced light olefin selectivity. The results of example 1 reported in Table 1 are novel and unexpected. Contrary to all prior teaching, there is no loss in ethylene+propylene selectivity with increasing pressure out to 120 psia, and the olefin ratio unexpectedly changes dramatically to favor the desired ethylene product.

What is claimed is:

1. A process for converting methanol or dimethyl ether to a product containing $C_2$ olefin, the process comprising the step of contacting a feed containing methanol or dimethyl ether and an aromatic compound which has a critical diameter less than the pore size of the zeolite catalyst and which is capable of alkylation by the methanol and/or dimethyl ether with a catalyst which comprises a zeolite having 10-ring intersecting channels and which has a Diffusion Parameter for 2,2-dimethylbutane of less than 100 $sec^{-1}$ when measured at a temperature of 120° C. and a 2,2-dimethylbutane pressure of 60 torr, the contacting step being conducted at a temperature of 370 to 480° C., a methanol or dimethyl partial pressure of 30 to 150 psia to provide $C_2$ olefin.

2. The process of claim 1, wherein said Diffusion Parameter of said catalyst is about 0.1–30 $sec^{-1}$.

3. The process of claim 1, wherein said contacting step is conducted at a temperature of 400 to 450° C. and a methanol or dimethylether partial pressure of 60 to 120 psia.

4. The process of claim 1, wherein said contacting step is conducted such that methanol or dimethylether conversion per pass is less than 95%.

5. The process of claim 1, wherein said methanol or dimethylether conversion per pass is 25–90%.

6. The process of claim 1, wherein said catalyst contains an oxide of phosphorus.

7. The process of claim 1, wherein said catalyst contains about 0.05 to about 20 wt % of an oxide of phosphorus on an elemental basis.

8. The process of claim 1, wherein said zeolite is ZSM-5 or ZSM-11.

* * * * *